United States Patent
Fung

(10) Patent No.: US 8,568,378 B2
(45) Date of Patent: *Oct. 29, 2013

(54) METHOD OF PACKAGING AN ABSORBENT ARTICLE AND ATTACHING THE ABSORBENT ARTICLE TO AN UNDERGARMENT

(75) Inventor: Paul Y. Fung, South River, NJ (US)

(73) Assignee: McNeill-PPC, Inc., Skillman, NJ (US)

( * ) Notice: Subject to any disclaimer, the term of this patent is extended or adjusted under 35 U.S.C. 154(b) by 724 days.

This patent is subject to a terminal disclaimer.

(21) Appl. No.: 12/512,147

(22) Filed: Jul. 30, 2009

(65) Prior Publication Data

US 2011/0028935 A1    Feb. 3, 2011

(51) Int. Cl.
  *A61F 13/15*    (2006.01)
  *A61F 13/20*    (2006.01)

(52) U.S. Cl.
  USPC ............. 604/385.02; 604/385.01; 604/385.03

(58) Field of Classification Search
  USPC ....................... 604/385.01–385.05
  See application file for complete search history.

(56) References Cited

U.S. PATENT DOCUMENTS

| | | | |
|---|---|---|---|
| 5,054,619 A | | 10/1991 | Muckenfuhs |
| 5,478,336 A | | 12/1995 | Pigneul |
| 5,748,336 A | * | 5/1998 | Kakutani ................ 382/252 |
| 5,769,837 A | * | 6/1998 | Parr .................... 604/390 |
| 5,993,430 A | * | 11/1999 | Gossens et al. ......... 604/385.02 |
| 6,036,679 A | * | 3/2000 | Balzar et al. ............. 604/387 |
| 6,063,065 A | * | 5/2000 | Costa .................. 604/385.02 |
| 6,074,376 A | * | 6/2000 | Mills .................... 604/390 |
| 6,293,932 B1 | | 9/2001 | Balzar et al. |
| 6,575,947 B1 | | 6/2003 | Tameishi et al. |
| 7,041,091 B2 | * | 5/2006 | Wheeler et al. ............ 604/391 |
| 7,427,277 B2 | * | 9/2008 | Woltman et al. ....... 604/385.201 |
| 2001/0056270 A1 | | 12/2001 | Mizutani et al. |
| 2005/0029144 A1 | | 2/2005 | Hermansson et al. |
| 2009/0105680 A1 | * | 4/2009 | Amiot et al. ............ 604/385.02 |

FOREIGN PATENT DOCUMENTS

| | | |
|---|---|---|
| EP | 1157680 | 11/2001 |
| WO | 9932059 | 7/1999 |
| WO | 2005/065605 | 7/2005 |

* cited by examiner

*Primary Examiner* — Michele M Kidwell

(57) ABSTRACT

A method of individually packaging an absorbent article and attaching the absorbent article to an undergarment including the steps of providing a tri-folded absorbent article having two end portions and an intermediate portion, providing a pouch containing the tri-folded absorbent article, opening the pouch to thereby expose a garment-facing surface of the intermediate portion of the absorbent article prior to exposing a garment facing surface of either of the end portions of the absorbent article.

11 Claims, 10 Drawing Sheets

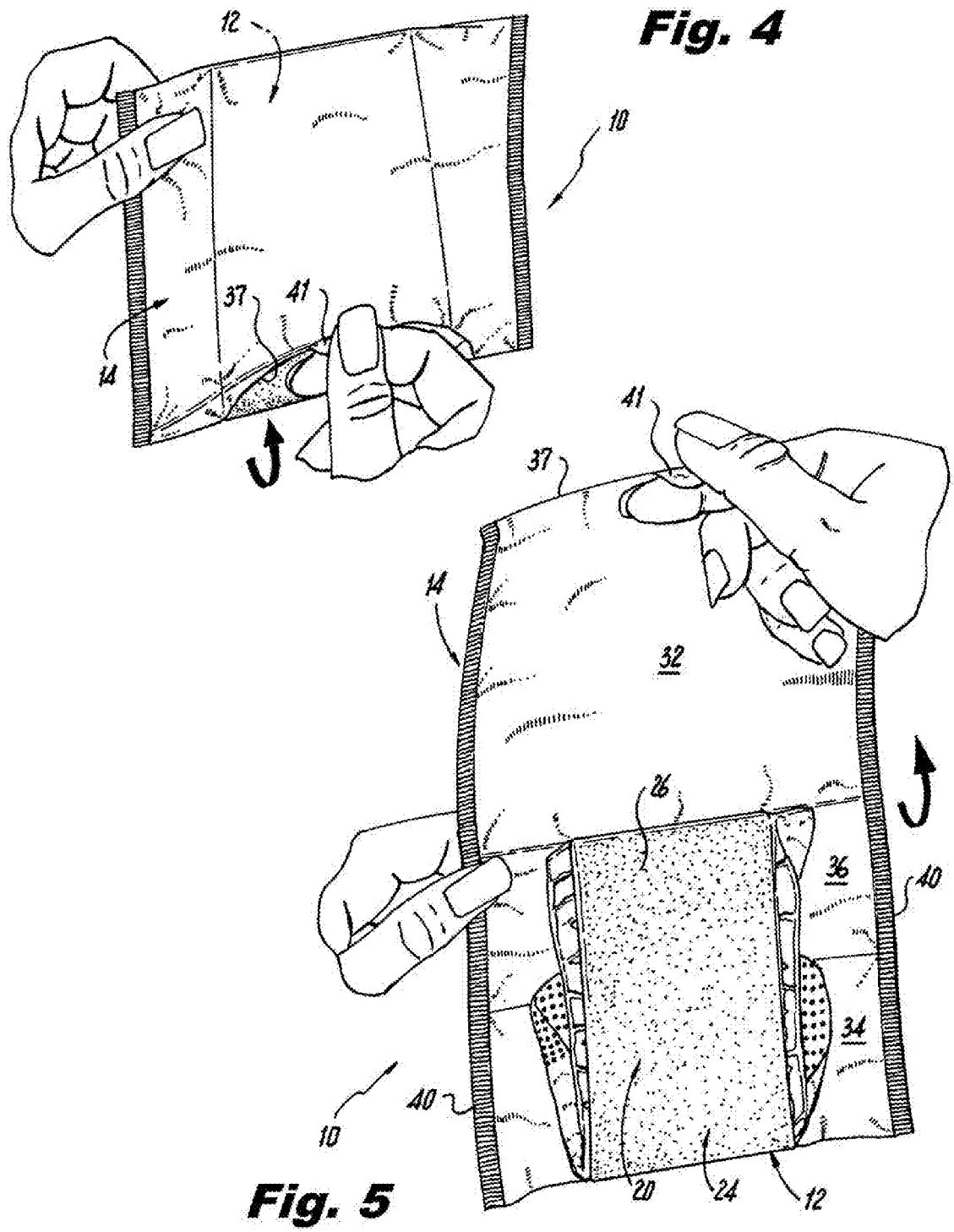

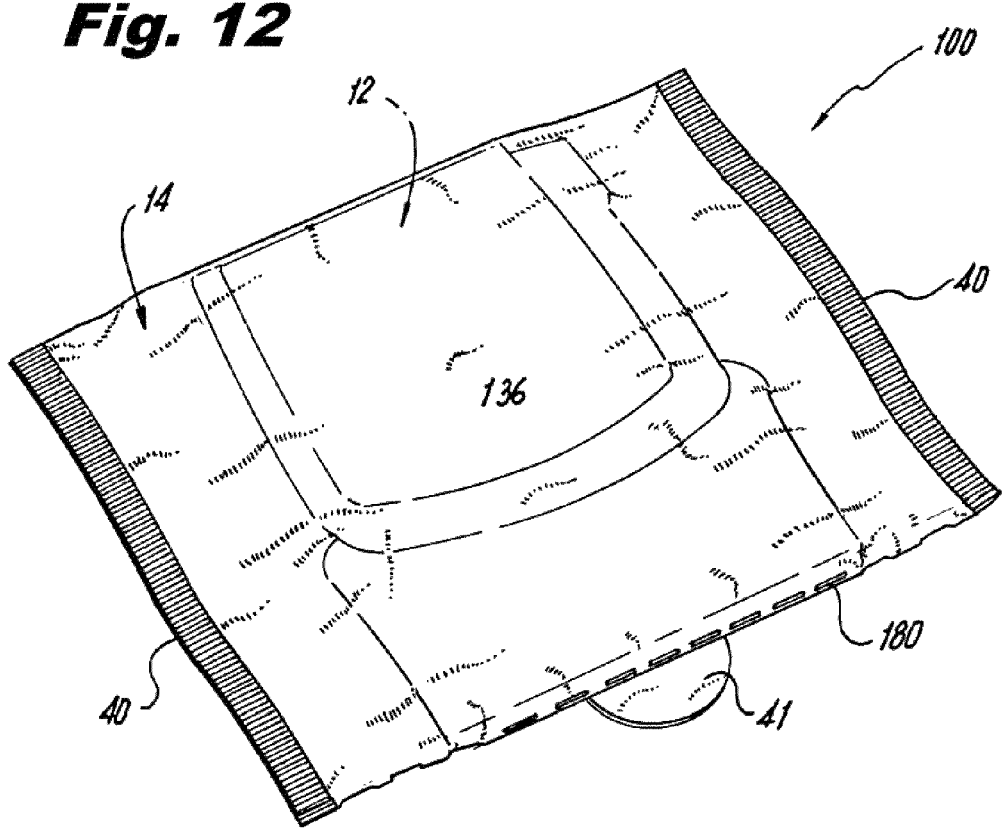
Fig. 12
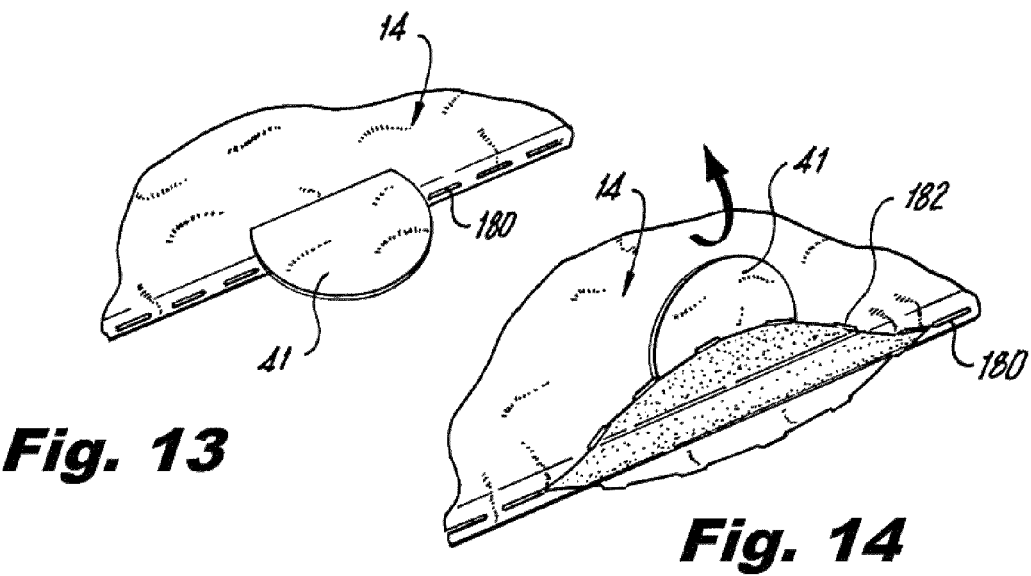
Fig. 13
Fig. 14

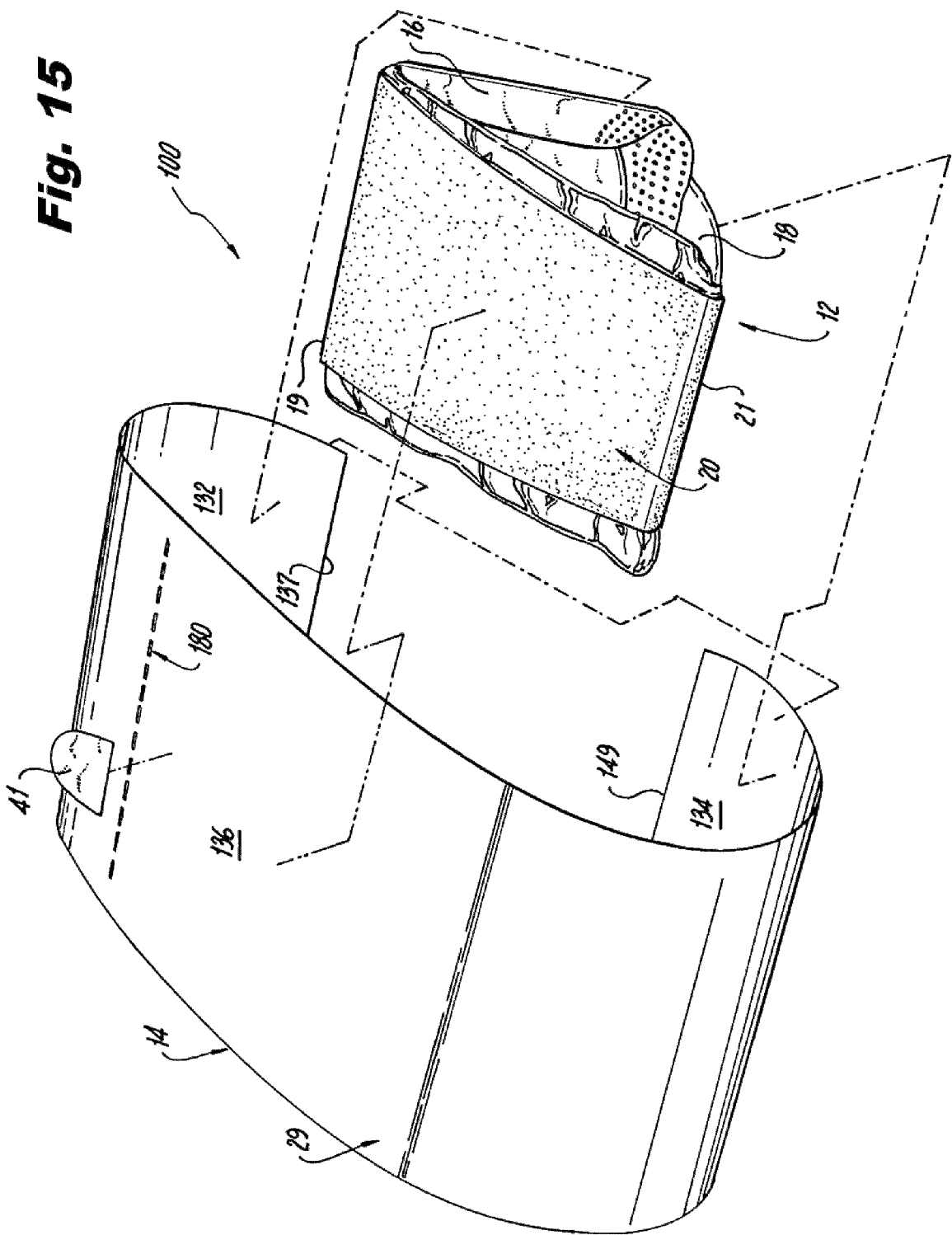

METHOD OF PACKAGING AN ABSORBENT ARTICLE AND ATTACHING THE ABSORBENT ARTICLE TO AN UNDERGARMENT

FIELD OF THE INVENTION

The present invention relates to individually packaged disposable absorbent articles, and in particular to a method of individually packaging an absorbent article and attaching the absorbent article to an undergarment.

BACKGROUND OF THE INVENTION

Individually packaged disposable absorbent articles are well known in the art. For example, feminine sanitary napkins are often sold in such a configuration. Commercially available sanitary napkins are commonly folded in three overlapping sections along the length of the napkin ("tri-folded") and such tri-folded napkin is arranged in a sealed pouch to thereby maintain the napkin sanitary prior to use. Sanitary napkins of this type conventionally include an adhesive arranged on a garment-facing side of the napkin ("garment attachment adhesive") to enable the user to attach the napkin to an undergarment during use. Prior to use, the garment attachment adhesive is covered by a removable release paper that is intended to protect the adhesive and prevent the garment attachment adhesive from adhering to the pouch prior to use. Alternatively, the release paper may by omitted, and the interior surface of the pouch may include a non-stick coating (e.g. silicone) to prevent the garment attachment adhesive from adhering to the pouch. When ready for use, a user removes the napkin from the pouch, unfolds the napkin, removes the release paper (if such paper is employed) and attaches the napkin to the undergarment.

The inventor of the present invention has discovered that a problem with the above described configuration is that the user must completely remove the napkin from the pouch, and remove the release paper if such release paper is present, prior to attaching the napkin to the undergarment. The above described process can be cumbersome and may cause the user to inadvertently attach the napkin at the wrong location in the undergarment and/or contaminate the garment attachment adhesive before the user attaches the napkin to the undergarment.

In view of the foregoing, the inventor has disclosed herein an improved method of individually packaging an absorbent article and method for attaching such absorbent article to an undergarment.

SUMMARY OF THE INVENTION

In view of the foregoing the present invention provides, according to a first aspect of the invention, a method of individually packaging an absorbent article and attaching the absorbent article to an undergarment including the steps of providing a tri-folded absorbent article including a garment-facing surface having a garment attachment adhesive, a body-facing surface, a first fold line, a second fold line, a first end portion, a second end portion, and an intermediate portion arranged between the first end portion and the second end portions, the first end portion being separated from the intermediate portion by the first fold line, the second end portion being separated from the intermediate portion by the second fold line, and the intermediation portion being located between the first fold line and the second fold line, providing a pouch for containing the tri-folded absorbent article, the pouch formed from a sheet material having a first terminal edge and a second terminal edge, opening the pouch along the first terminal edge of the sheet material and lifting the sheet material to expose a garment-facing surface of the intermediate portion of the article prior to exposing the garment-facing surface of the first end portion and the garment-facing surface of the second end portion.

The present invention provides, according to a second aspect of the invention, a method of individually packaging an absorbent article and attaching the absorbent article to an undergarment including the steps of providing a tri-folded absorbent article including a garment-facing surface, a body-facing surface, a first fold line, a second fold line, a first end portion, a second end portion, and an intermediate portion arranged between the first end portion and the second end portions, the first end portion being separated from the intermediate portion by the first fold line, the second end portion being separated from the intermediate portion by the second fold line, and the intermediation portion being located between the first fold line and the second fold line, providing a pouch for containing the tri-folded absorbent article, the pouch formed from a sheet material having a first terminal edge, a second terminal edge and a line of weakness arranged between the first terminal edge and the second terminal edge, opening the pouch along the line of weakness and lifting the sheet material to expose a garment-facing surface of the intermediate portion of the article prior to exposing the garment-facing surface of the first end portion and the garment-facing surface of the second end portion.

BRIEF DESCRIPTION OF THE DRAWINGS

FIGS. 4-11 depict the manner in which the absorbent article is removed from the pouch and applied to an undergarment;

FIG. 12 is a bottom perspective view of an individually packaged absorbent article assembly according to a second embodiment of the present invention showing the exterior surface of the pouch that forms part of the assembly;

FIG. 13 is a detailed top perspective view of a portion of the individually packaged absorbent article assembly shown in FIG. 12;

FIG. 14 is detailed view of a portion of the individually packaged absorbent article assembly shown in FIG. 13 depicting the manner in which pouch is opened to obtain access to the absorbent article; and FIG. 15 is a partially exploded view of the of the absorbent article assembly shown in FIG. 12 revealing the sheet of material that forms the pouch and the absorbent article contained within such pouch.

DETAILED DESCRIPTION OF THE INVENTION

Figure 1:
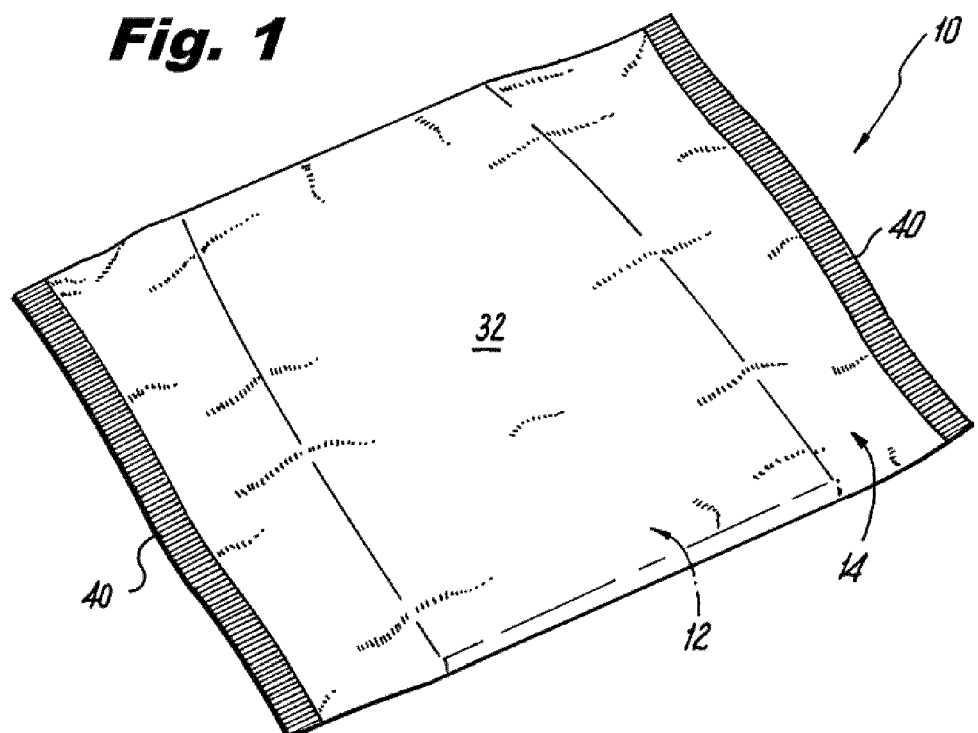
FIG. 1 is a top perspective view of an individually packaged absorbent article assembly according to a first embodiment of the present invention showing the exterior surface of the pouch that forms part of the assembly.

Referring now to the drawings there is shown an individually packaged disposable absorbent article assembly embodying the teachings of the present invention. As used herein "disposable absorbent articles" includes articles such as sanitary napkins, pantiliners, absorbent products for incontinence, and other disposable absorbent articles worn close to a wearer's body. Although the invention will be described herein with reference to a sanitary napkin, the invention may be utilized with other disposable sanitary absorbent articles such as absorbent products for incontinence, diapers, pantiliners and the like.

Figure 2:
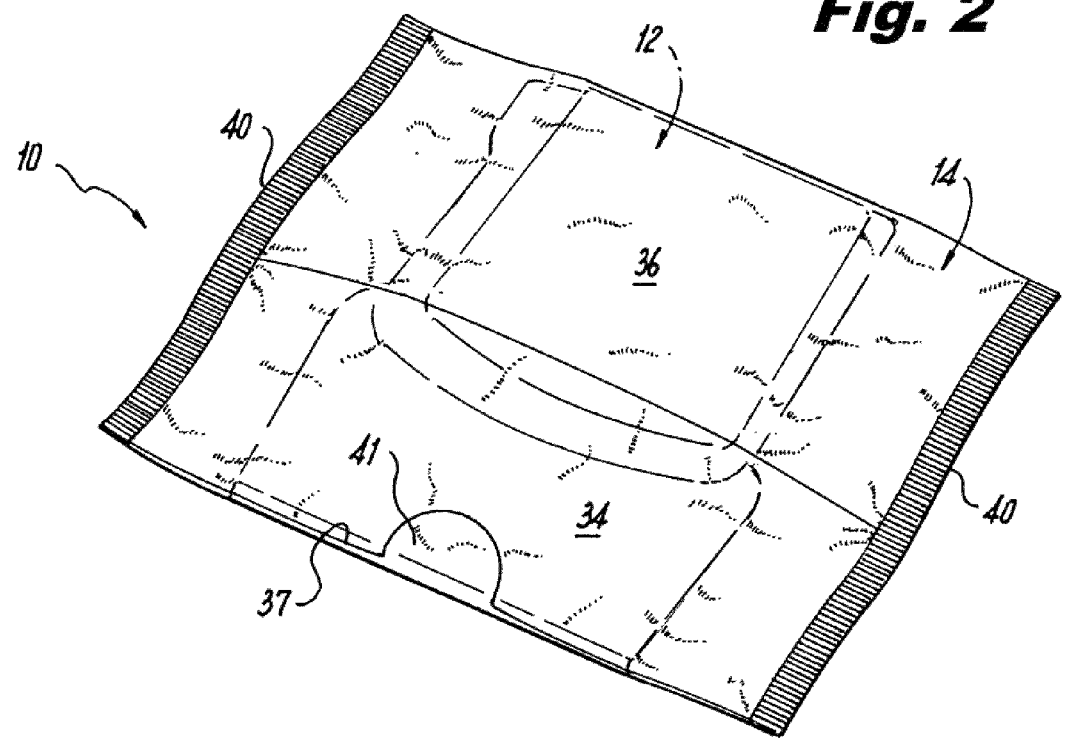
FIG. 2 is bottom perspective view of an individually packaged absorbent article assembly according to the present invention.
Figure 3:
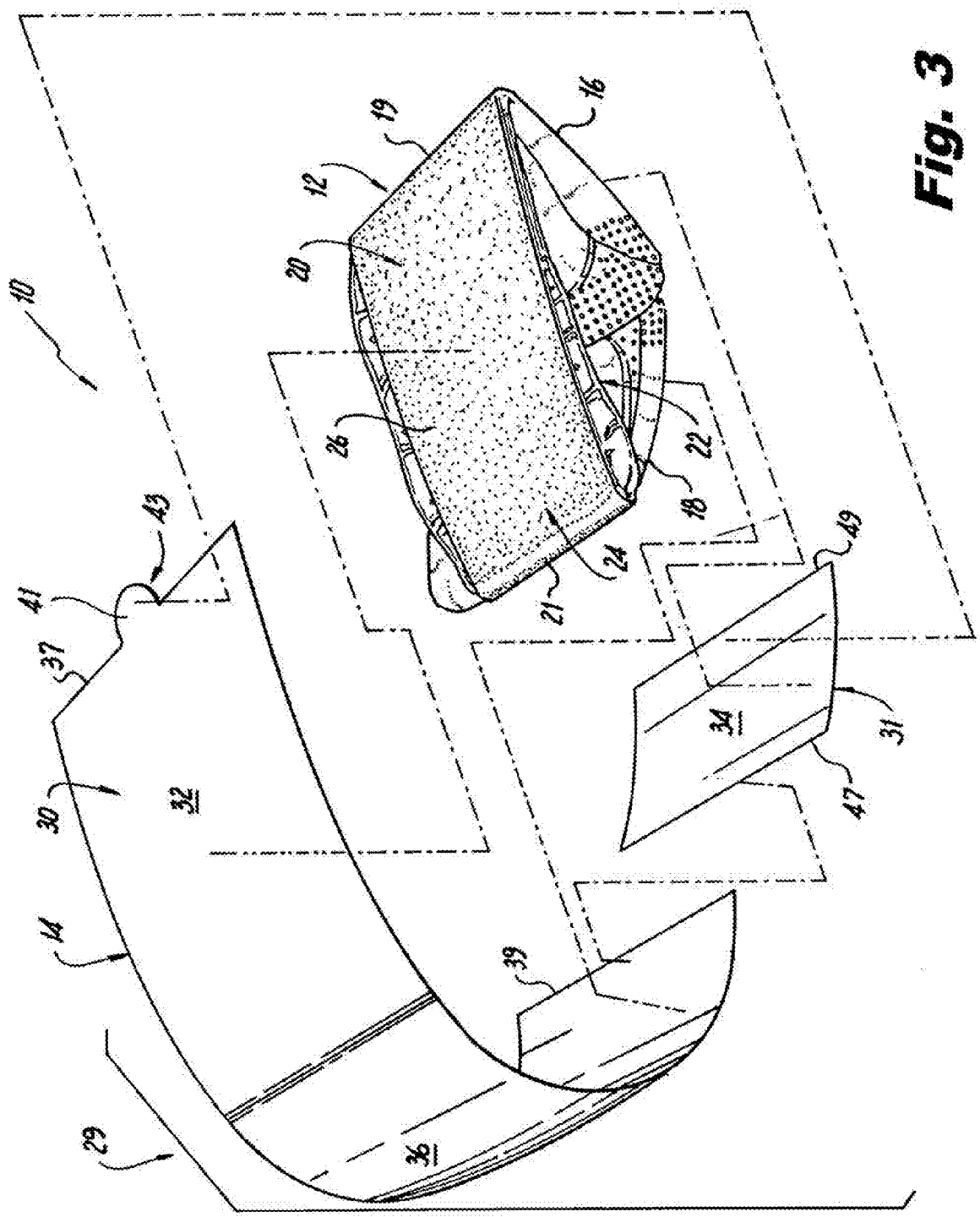
FIG. 3 is a partially exploded view of the of the absorbent article assembly shown in FIGS. 1 and 2 revealing the first and second sheets of material that define the pouch and the absorbent contained within such pouch.
Figure 6:
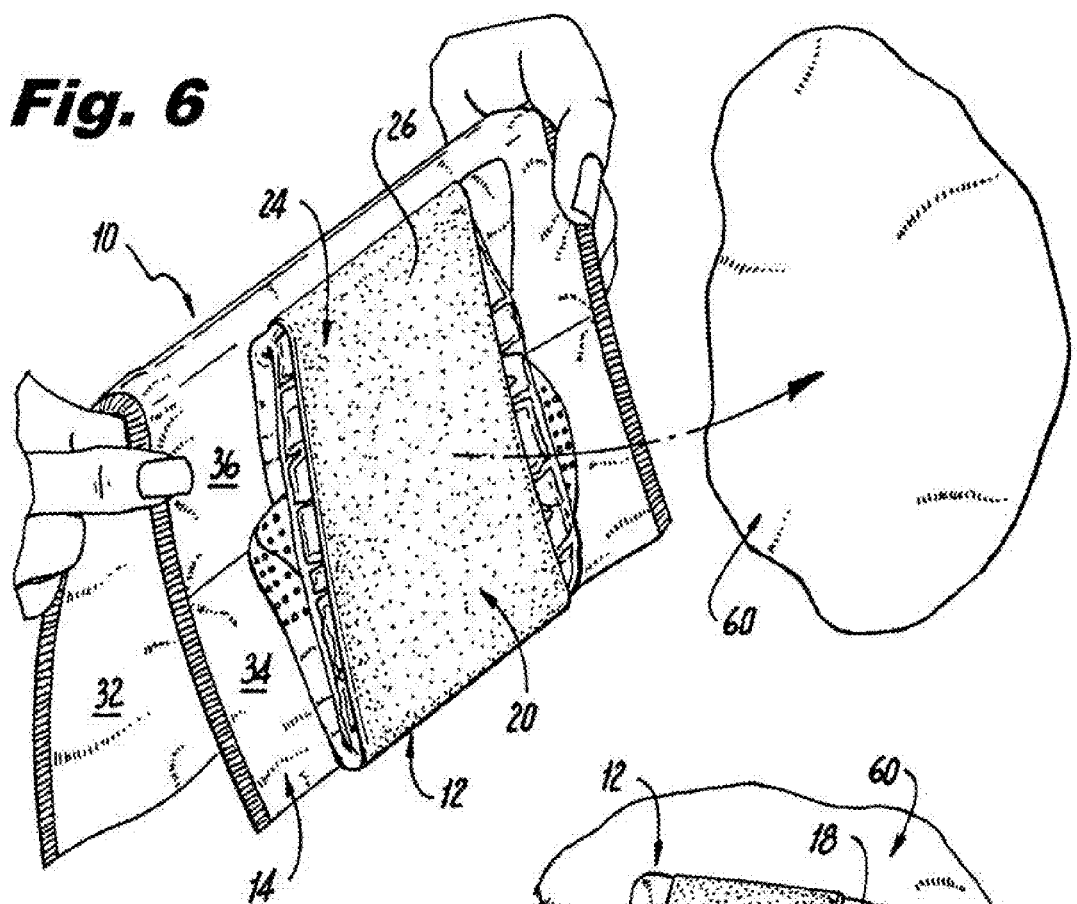

An individually packaged absorbent article assembly 10 according to a first embodiment of the present invention is shown in FIGS. 1-3. The individually packaged absorbent article assembly 10 generally includes a sanitary napkin 12 and a pouch 14.

Prior to removal from the pouch 14, the sanitary napkin 12 is tri-folded such that three portions of the napkin 12 are defined. Specifically, referring to FIG. 3, the napkin 12 in its folded state prior to use includes a first end portion 16, a second end portion 18, and an intermediate portion 20 arranged between the end portions 16 and 18. The first end portion 16 is separated from the intermediate portion 20 by fold line 19 and the second end portion 18 is separated from the intermediate portion 20 by fold line 21. The napkin 12 further includes a body-facing surface 22 and a garment-facing surface 24. The terms "body-facing" and "garment-facing" as used herein are intended to indicate the final orientation of the napkin after the napkin has been attached to an undergarment by the user.

As shown in FIG. 3, the first end portion 16 is folded toward the body-facing surface 22 and then the second end portion 18 is folded on top of and in overlapping relationship to the first end portion 16. The napkin 12 also includes a garment attachment adhesive 26 that is applied to the garment-facing surface 24 of the napkin that functions to attach the napkin 12 to an undergarment during use.

In the specific embodiment of the invention shown in FIGS. 1-3, the pouch 14 is defined by two lengths of a sheet material 29 that are attached to one another to form the final pouch 14. However, the pouch 14 could alternatively be formed from a single length of the sheet material 29. The sheet material 29 may be a plastic film sheet or a paper sheet material. The paper or plastic film sheet is coated on its inwards facing surface thereof with a coating of silicone polymer to prevent the adhesive 26 on the garment-facing surface of the napkin 12 from adhering to the pouch 14. Other non-stick coatings may be employed provided that they effectively prevent the napkin 12 from adhering to the pouch 14.

In the specific embodiment of the invention shown in FIGS. 1-3, the pouch is formed by a first length of sheet material 30 and a second length of sheet material 31. The first length of material 30 defines a first end section 32 of the sheet material 29 and the second length of material 31 defines a second end section 34 of the sheet material 29. The first length of material 30 further defines an intermediate section 36 of the sheet material 29 arranged between the end sections 32 and 34. The first length of material 30 includes a first terminal transverse edge 37 and a second terminal transverse edge 39. The second length of material 31 includes a first terminal transverse edge 47 and a second terminal transverse edge 49.

As shown in FIG. 3 the first length of material 30 partially overlaps the second length of material 31 adjacent terminal edges 39 and 47 and the two lengths of material are permanently secured to one another by a strip of adhesive or the like. Thus, in the final pouch configuration the sheet material 29 has two terminal edges, i.e. terminal edges 37 and 49.

As shown in FIG. 3, the first end section 32 of the sheet material 29 extends over and corresponds in location to the intermediate portion 20 of the napkin 12. The intermediate section 36 of the sheet material 29 extends over and corresponds in location to the second end portion 18 of the napkin 12. The second end section 34 of the sheet material 29 extends over and corresponds in location to the first end portion 16 of the napkin 12.

It is noted that in the final pouch 14 configuration the first terminal edge 37 of the first length of material 30 is substantially aligned with the fold line 19 of the napkin 12 that separates the intermediate portion 20 of the napkin 12 from the first end portion 16 of the napkin 12.

Along the first terminal edge 37, the first length of material 30 may optionally be provided with a tab 41. The tab 41 may be formed from the first length of material 30 or may constitute a separate piece of material permanently attached to the first length of material 30. As show in FIG. 2, the tab 41 overlaps the end section 34 of the pouch 14 and is secured to the external surface of the end section 34 by adhesive arranged on a bottom surface 43 of the tab 41. The adhesive provided on the bottom surface 43 of the tab 41 should be selected so as to enable a user to selectively open the pouch 14 by pulling on the tab 41, as will be described herein in greater detail below.

As shown in FIGS. 1 and 2, the pouch 14 also includes side seams 40 defined by embossments running along and defining opposite longitudinal edge zones of the pouch. The side seams 40 function to seal the overlapping portions of the sheet material 29 and thereby form a sealed enclosure for the napkin 12. The embossments may be formed by any suitable known means to provide such embossments, such as heated embossing rolls or the like. Alternatively, in lieu of embossments, other means such as glue or tape may be used to seal the pouch.

The manner of deploying the napkin 12 from the pouch 14, and attachment of the napkin to an undergarment 60 of a user, will now be described with reference to FIGS. 4-11. As shown in FIGS. 4 and 5 the user first grasps the tab 41 and pulls the tab 41 to separate the same from the external surface of the end section 34 of the pouch 14. As the user pulls the tab 41 and lifts the first end section 32 of the pouch 14, the embossments defining the side seams 40 separate thereby exposing the intermediate portion 20 of the napkin 12, and more specifically exposing the garment-facing surface 24 of the intermediate portion 20. Thereafter, as shown FIG. 6, the user may then attach the intermediate portion 20 of the napkin 12 to the undergarment 60 with the garment-facing surface 24 of the napkin 12 in abutting relationship to the undergarment 60.

Figure 7:
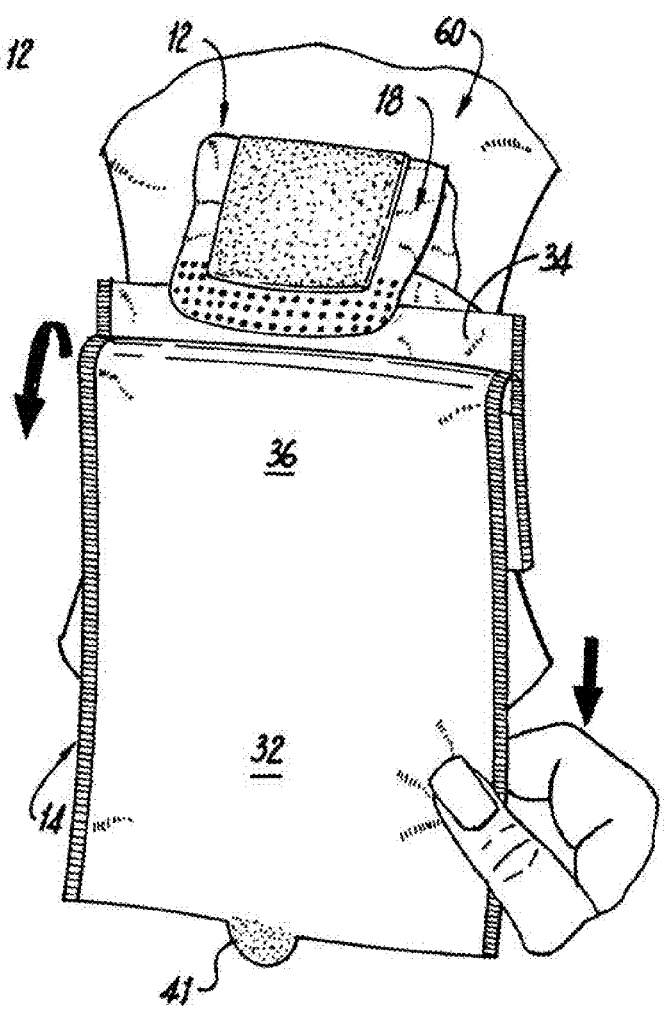
Figure 8:
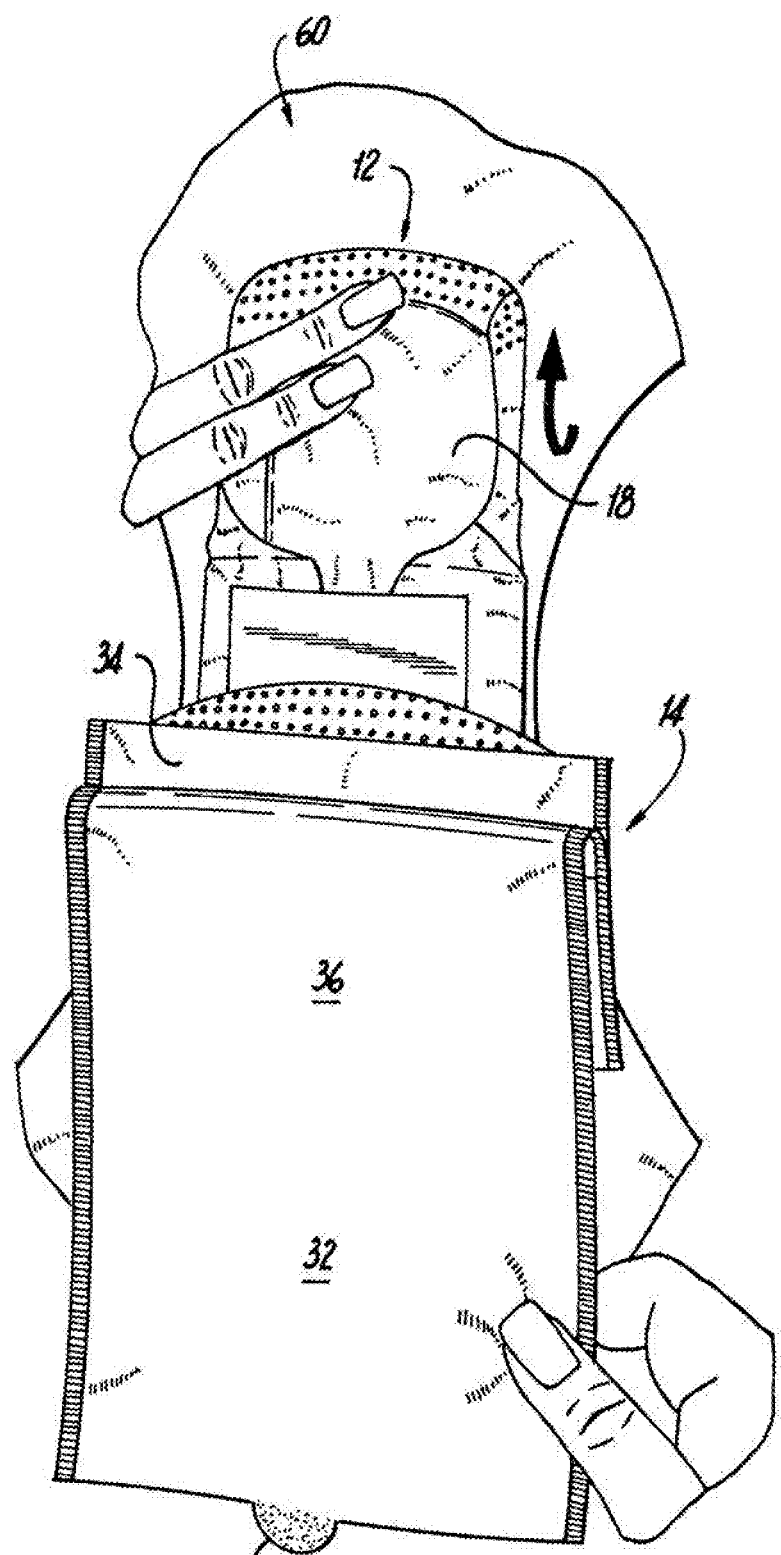
Figure 9:
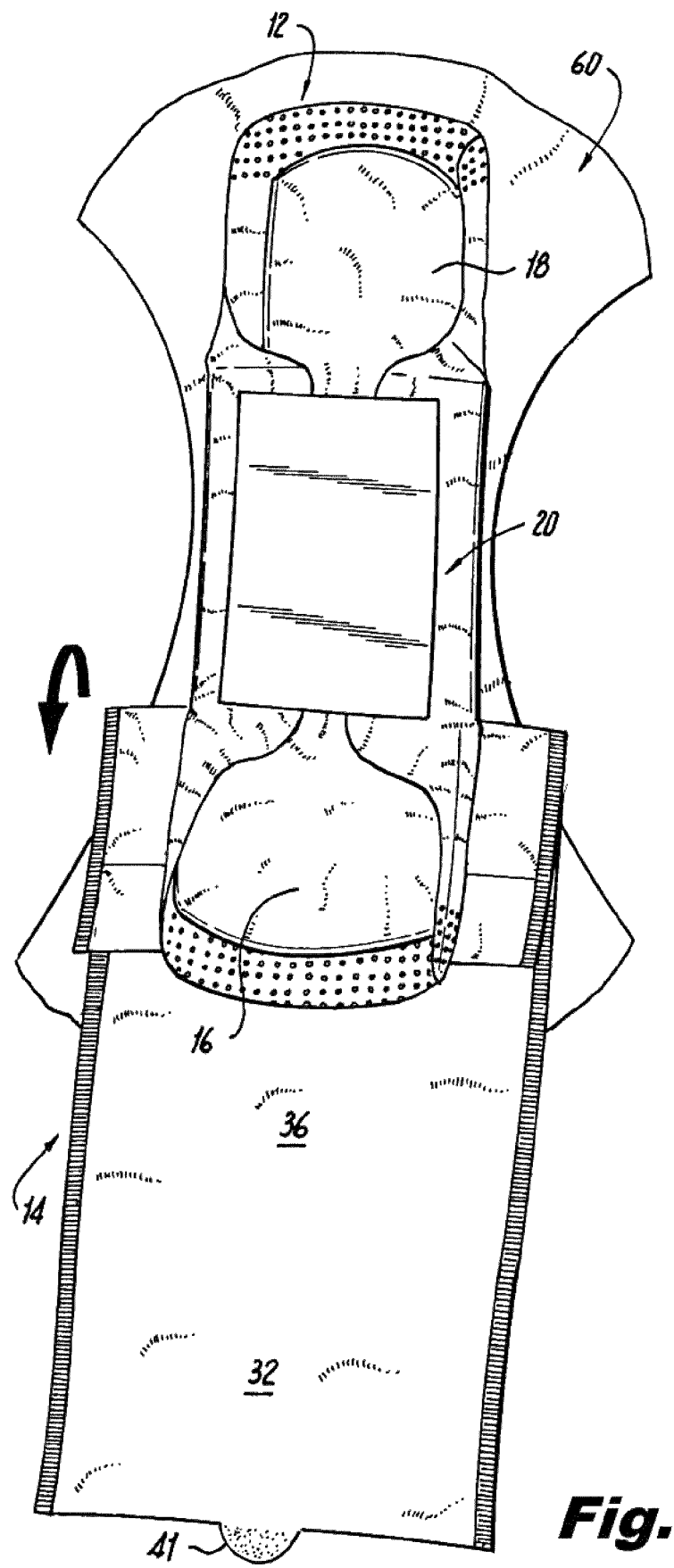
Figure 10:
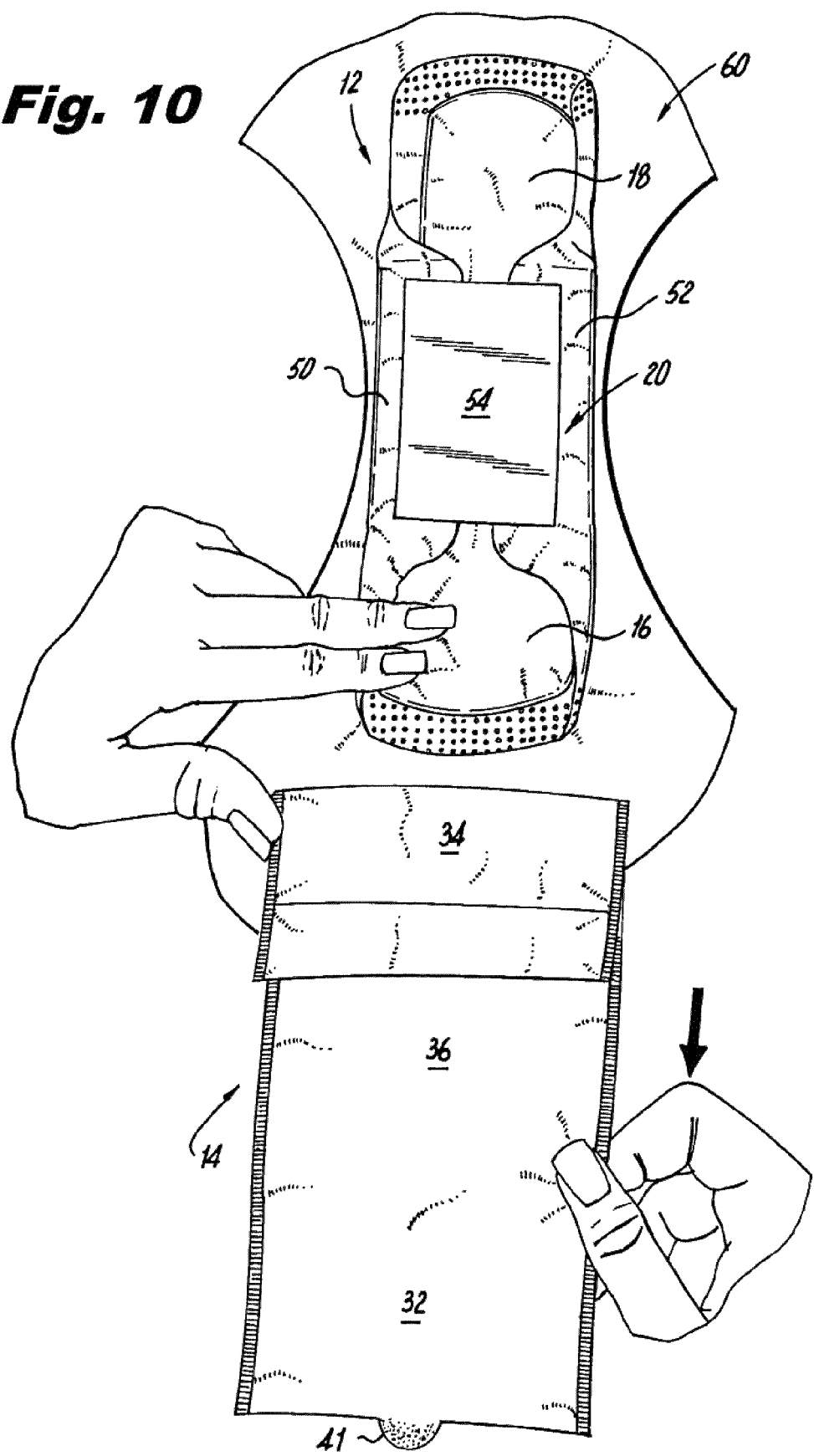

As the user continues to pull on the tab 41, and/or the portion of the pouch 14 now separated from the napkin 12, the second end portion 18 of the napkin is released from the pouch 14 as shown in FIG. 7. Thereafter, the user may then attach the second end portion 18 of the napkin to the undergarment 60 as shown in FIG. 8. As the user continues to pull on the tab 41, and/or the portion of the pouch 14 now separated from the napkin 12, the first end portion 16 of the napkin 12 is release from the pouch as shown in FIG. 9. Thereafter, the user may then attach the first end portion 16 of the napkin 12 to the undergarment 60 as shown in FIG. 10.

Figure 11:
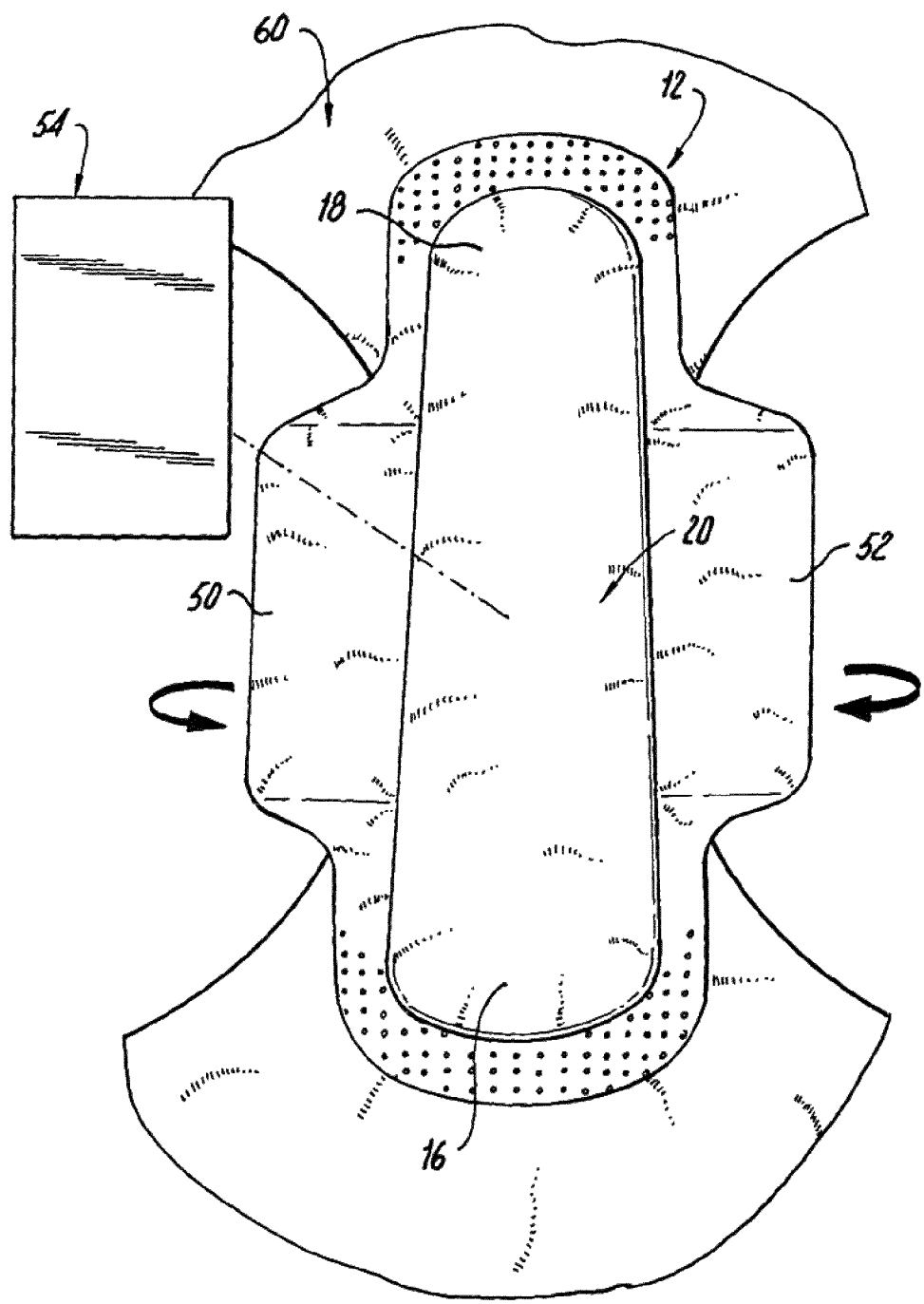

The napkin 12 may optionally be provided with wings 50 and 52 that extend out from the main body of the napkin 12 and are adapted to be folded over the edges of the undergarment 60 and attached to the crotch portion of the undergarment 60 by means of adhesive provided on the garment-facing surface of the wings 50 and 52. Prior to deployment of the wings 50 and 52 the wings 50 and 52 may be folded toward the body-facing surface 22 of the napkin 12 and the adhesive on the wings 50 52 may be covered by a release paper 54. When the user is ready to attach the wings 50 and 52 to the undergarment the release paper 54 may be removed and the wings 50 and 52 folded around the edges of the undergarment 60 and attached to the crotch portion of the undergarment 60, as shown in FIG. 11

It is noted that that the individually packaged absorbent article assembly 10 as described above enables the intermediate portion 20 of the napkin, and particularly the garment-facing surface 20 thereof, to be first exposed prior to exposing the garment-facing surfaces of the other portions of the napkin 12. This enables the user to easily attach the intermediate portion 20 of the napkin to the undergarment before the other portions of the napkin are deployed form the pouch 14. This significantly simplifies the attachment process and represents a significant improvement over prior art assemblies.

Another embodiment of an individually packaged absorbent article assembly 100 will now be described with reference to FIGS. 12-15. In those instances where the same or similar structural elements are present in the second embodiment of the invention as those described above with regard to the first embodiment the same or similar reference numerals will be employed. The individually packaged absorbent article assembly 100 generally includes a sanitary napkin 12 and a pouch 14.

In the specific embodiment of the invention shown in FIGS. 12-15, the pouch 14 is defined by a single piece of sheet material 29. The sheet material may be a plastic film sheet or a paper sheet material. The sheet material 29 includes a first end section 132, a second end section 134, and an intermediate section 136 arranged between the end sections 132 and 134.

In the second embodiment of the invention 100, the intermediate section 136 of the sheet material 29 extends over and corresponds in location to the intermediate portion 20 of the napkin 12. The second end section 134 of the sheet material 29 extends over and corresponds in location to the second end portion 18 of the napkin 12. The first end section 132 of the sheet material 29 extends over and corresponds in location to the first end portion 16 of the napkin 12. The sheet material 29 includes a first terminal edge 137 and a second terminal edge 149. The sheet material 20 is also provided with a score line or other line of weakness 180 arranged between the first terminal edge 137 and the second terminal edge 149.

It is noted that in the final pouch 14 configuration the score line 180 is substantially aligned with the fold line 19 of the napkin 12 that separates the intermediate portion 20 of the napkin 12 from the first end portion 16 of the napkin 12. The pouch 14 may optionally be provided with a tab 41 that is formed from a separate piece of material that is permanently attached to the pouch in a location adjacent the score line 180. As shown in FIG. 14, when a user desires to open the pouch 14 the user grasps the tab 41 and pulls the tab in an upward direction causing the pouch 14 to open along the score line 180, i.e. by forming a "free end" 182 of the sheet material 29 along the score line 180.

As shown in FIG. 12, the side seams of the pouch 14 are designated by the numeral 40 and are defined by embossments running along and defining opposite longitudinal edge zones of the pouch. The side seams 40 function to seal the overlapping portions of the sheet material 29. As shown in FIG. 15, the second end section 134 of the sheet material partially overlaps the first end section 132 of the sheet material adjacent terminal edges 149 and 137 and the two ends of the sheet material 29 are permanently secured to one another by a strip of adhesive or the like. In this manner, the pouch 14 provides a sealed enclosure for the tri-folded napkin 12 prior to use of the napkin 12.

The manner of deploying the napkin 12 from the pouch 14 in the individually packaged absorbent article assembly 100 is substantially identically to the manner employed in the first embodiment of the invention 10 described above with reference to FIGS. 4-11. However, with the absorbent article assembly 100 the user initiates opening the pouch 14 by opening the pouch along the score line 180. Specifically, the user grasps the tab 41 and pulls the tab 41 in an upward direction to thereby open the pouch 14 along the score line 180.

It is noted that that the individually packaged absorbent article assembly 100 as described above, like the first embodiment of the invention 10, enables the intermediate portion 20 of the napkin, and in particularly the garment-facing surface 20 thereof, to be first deployed prior to the deployment of the other portions of the napkin 12. This enables the user to easily attach the intermediate portion 20 of the napkin to the undergarment before the other portions of the napkin are deployed form the pouch 14. This significantly simplifies the attachment process and represents a significant improvement over prior art assemblies.

I claim:

1. A method of individually packaging an absorbent article and attaching the absorbent article to an undergarment comprising the steps of:
providing a tri-folded absorbent article including a garment-facing surface having a garment attachment adhesive, a body-facing surface, a first fold line, a second fold line, a first end portion, a second end portion, and an intermediate portion arranged between the first end portion and the second end portions, the first end portion being separated from the intermediate portion by the first fold line, the second end portion being separated from the intermediate portion by the second fold line, and the intermediation portion being located between the first fold line and the second fold line;
providing a pouch for containing the tri-folded absorbent article, the pouch formed from a sheet material having a first terminal edge and a second terminal edge; and
opening the pouch along the first terminal edge of the sheet material and lifting the sheet material to expose a garment-facing surface of the intermediate portion of the article prior to exposing the garment-facing surface of the first end portion and the garment-facing surface of the second end portion.

2. The method according to claim 1, further comprising:
attaching the garment-facing surface of the intermediate portion to an undergarment.

3. The method according to claim 2, further comprising:
lifting the portion of the sheet material released from napkin to expose a garment-facing surface of the second end portion of the article prior to exposing the garment-facing surface of the first end portion.

4. The method according to claim 3, further comprising:
attaching the garment-facing surface of the second end portion to the undergarment.

5. The method according to claim 4, further comprising:
lifting the portion of the sheet material released from the napkin to expose a garment-facing surface of the first end portion of napkin.

6. The method according to claim 5, further comprising:
attaching the garment-facing surface of the first end portion to the undergarment.

7. The method according to claim 6, wherein the sheet of material includes a first end section, an intermediate section and a second end section, and prior to opening the pouch the first end section of the sheet material extends over and corresponds in location to the intermediate portion of the absorbent article, the intermediate section of the sheet material extends over and corresponds in location to the second portion of the absorbent article, and the second end section of the sheet material extends over and corresponds in location to the first end portion of the napkin.

8. The method according to claim 7, further comprising: providing a tab that extends from the first end section and is releasably attached to the second end section of the sheet material.

9. The method according to claim 8, further comprising: providing the pouch with side seams defined by a plurality of embossments to thereby seal overlapping portions of the sheet material.

10. The method according to claim 9, further comprising: grasping the tab and lifting the tab upward to detach the tab from the second end section and open the pouch along the first terminal edge of the sheet material.

11. The method according to claim 1, wherein the first terminal edge of the sheet material is substantially aligned with the first fold line.

\* \* \* \* \*